(12) United States Patent
Hsu et al.

(10) Patent No.: US 7,067,467 B2
(45) Date of Patent: Jun. 27, 2006

(54) AQUEOUS PERBORATE BLEACH COMPOSITION

(75) Inventors: Feng-Lung Gordon Hsu, Tenafly, NJ (US); Yun Peng Zhu, Fairlawn, NJ (US); Kimball James Woelfel, Fort Lee, NJ (US); Mohammad Hosseini-Nejad, East Hanover, NJ (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 476 days.

(21) Appl. No.: 10/323,492

(22) Filed: Dec. 19, 2002

(65) Prior Publication Data

US 2004/0121931 A1 Jun. 24, 2004

(51) Int. Cl.
*C11D 3/395* (2006.01)

(52) U.S. Cl. .................. 510/378; 510/303; 510/370

(58) Field of Classification Search ............ 510/303, 510/370, 375, 378
See application file for complete search history.

(56) References Cited

U.S. PATENT DOCUMENTS

| | | | |
|---|---|---|---|
| 2,317,297 A | | 4/1943 | Omohundro et al. ......... 167/93 |
| 3,130,165 A | * | 4/1964 | Brocklehurst et al. ........ 252/99 |
| 3,850,831 A | | 11/1974 | Hellsten et al. ............... 252/99 |
| 4,317,814 A | | 3/1982 | Laso ......................... 424/130 |
| 4,526,709 A | | 7/1985 | Boskamp et al. ............. 252/527 |
| 4,603,045 A | * | 7/1986 | Smigel ........................ 424/52 |
| 4,690,776 A | | 9/1987 | Smigel .................... 252/315.3 |
| 4,959,179 A | | 9/1990 | Aronson et al. ............. 252/135 |
| 5,089,163 A | | 2/1992 | Aronson et al. ............. 252/135 |
| 5,160,655 A | | 11/1992 | Donker et al. ................ 252/95 |
| 5,419,847 A | | 5/1995 | Showell et al. ............. 252/100 |
| 5,458,802 A | | 10/1995 | Sanderson et al. ...... 252/186.31 |
| 5,468,410 A | | 11/1995 | Angevaare et al. ........... 252/95 |
| 5,468,414 A | | 11/1995 | Panandiker et al. ......... 252/135 |
| 5,480,576 A | | 1/1996 | Gary et al. ................... 252/95 |
| 5,719,117 A | | 2/1998 | Falk et al. .................. 510/475 |
| 5,723,434 A | | 3/1998 | Falk et al. .................. 510/475 |
| 5,922,083 A | | 7/1999 | Biscarini et al. ............... 8/137 |
| 6,482,786 B1 | | 11/2002 | Del Duca et al. ........... 510/309 |
| 2003/0129148 A1 | | 7/2003 | Chen ........................... 424/53 |

FOREIGN PATENT DOCUMENTS

| | | |
|---|---|---|
| EP | 080 748 | 7/1985 |
| EP | 181 041 | 2/1991 |
| EP | 717 102 | 6/1996 |
| EP | 1 038 947 | 9/2000 |
| WO | 91/12308 | 8/1991 |
| WO | 95/10588 | 4/1995 |

OTHER PUBLICATIONS

Co-pending application: Applicant: Zhu et al., Filed: Dec. 19, 2002.
Pct International Search Report in a PCT application: PCT/EP 03/13081.
Japanese Abstract 2001104968—Published Apr. 17, 2002.

* cited by examiner

*Primary Examiner*—Gregory Delcotto
*Assistant Examiner*—John M Petruncio
(74) *Attorney, Agent, or Firm*—Rimma Mitelman

(57) ABSTRACT

Aqueous compositions comprising a perborate salt and a polyol. The advantageous properties of the composition include increased solubility of the perborate salt, increased available oxygen stability in an aqueous environment, and the capacity to increase the pH upon the dilution. The compositions are useful for bleaching various surfaces, especially in laundry cleaning.

19 Claims, No Drawings

AQUEOUS PERBORATE BLEACH COMPOSITION

FIELD OF THE INVENTION

The present invention relates to bleaching compositions comprising a perborate salt and a polyol and to methods of using such compositions.

BACKGROUND OF THE INVENTION

Perborate salts (also sometimes mentioned hereinbelow as "perborate") are known bleaches. Perborate, when dissolved in water, forms hydrogen peroxide, which in turn delivers oxygen bleaching benefit. Perborate in aqueous laundry detergent compositions has been described. See, for instance, Del Duka et al., U.S. Pat. No. 6,482,786; European patents EP0080748, EP0181041; Biscarini, U.S. Pat. No. 5,922,083; Showell et al., U.S. Pat. No. 5,419,847 and Boskamp, U.S. Pat. No. 4,526,709. Sanderson et al., U.S. Pat. No. 5,458,802 describes non-aqueous formulations containing perborate for laundry use. EP 0717102 describes a liquid automatic dishwashing detergent containing, among other ingredients, perborate and polyol, the free moisture content of the composition said to be kept at the minimum. Smigel (U.S. Pat. Nos. 4,603,045 and 4,690,776) describes toothpastes containing water, perborate, and polyol.

Some of the disclosures cited above also mention polyol or mixtures of polyol with boric acid or borate salts, which are known enzyme stabilization systems. Mixtures of polyol with boric acid or borates protect the enzyme in the composition by the so called "pH jump" mechanism. See also Panandiker et al., U.S. Pat. No. 5,468,414; Aronson et al., U.S. Pat. No. 5,089,163; Aronson et al., U.S. Pat. No. 4,959,179; Falk et al., U.S. Pat. No. 5,719,117; and Falk et al., U.S. Pat. No. 5,723,434.

A pH jump system functions by adjusting the pH of the wash liquor. To achieve the required pH regimes, a pH jump system is employed to keep the pH of the product low for enzyme stability yet allow it to become moderately high in the wash for detergency efficacy. One such system is borax/polyol complex. Upon dilution, the complex dissociates, liberating free borate to raise the pH. Such borax or boric acid complexes with polyol, however, do not generate perborate bleach and are not bleach systems.

The use of perborate in aqueous compositions has been hampered by the limited solubility of perborate in water, the challenge being to incorporate sufficient amounts of perborate into an aqueous composition to deliver the bleaching benefit and to avoid the presence of undissolved perborate in the composition.

SUMMARY OF THE INVENTION

The present invention includes a bleach composition comprising:
(a) from about 1% to about 44%, by weight of the composition, of a perborate salt as a source of oxygen bleach;
(b) from about 1% to about 44%, by weight of the composition, of a polyol, wherein the molar ratio of the perborate salt to the polyol is from about 1:10 to about 10:1;
(c) and water in an amount of at least 55%, by weight of the composition.

The present invention is based at least in part on the surprising discovery that the mixture of perborate with polyol results in an increased solubility of perborate in water. Furthermore, it has been discovered by the present inventors that, despite the increased solubility of the perborate in water (which in turn should result in increased levels of peroxide), the resulting peroxide is substantially more stable in the inventive perborate/polyol/water compositions compared to peroxide/borax/sorbitol/water compositions. A further advantage of the inventive compositions is that they, surprisingly, achieve the pH jump effect to an even greater degree than borax/polyol compositions.

The invention also includes methods of using the compositions to bleach surfaces, to clean laundry, and to obtain a pH jump upon the dilution.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the final aqueous composition, unless otherwise specified.

It should be noted that in specifying any range of concentration, any particular upper concentration can be associated with any particular lower concentration.

For the avoidance of doubt the word "comprising" is intended to mean "including" but not necessarily "consisting of" or "composed of." In other words, the listed steps or options need not be exhaustive. "Liquid" as used herein means that a continuous phase or predominant part of the composition is liquid and that a composition is flowable at 20° C. (i.e., suspended solids may be included). Both liquid and pourable gels are included.

Perborate Salt

The inventive compositions include a perborate salt as a source of bleach. Suitable perborate salts include but are not limited to tetrahydrate, monohydrate and trihydrate salts, since these forms are commercially available. Also suitable for use in the invention are superborate salts as described in U.S. Pat. No. 5,458,802 incorporated by reference herein. Super-perborates are included in the term "perborate" as used herein. The superperborates are defined by having an available oxygen (Avox) content of greater than 16.1%, preferably an Avox of between 16.5 and 30%, more preferably between 17 and 25%. Many superperborates have an empirical chemical formula of the type $Na_xB_yO_z.nH_2O$ where x, y, z, and n represent the number of moles of the respective elements in the molecular formula. The ratio of x:y is in many instances in the range from about 0.5 to about 1.2:1, and is often 1:1. The value of x often lies in the range from 1 to 4, the value of y often lies in the range from 1 to 5, the value of z often lies in the range from 2 to 15 and the value of n often lies in the range from 1 to 5. The ratio of Avox is y is greater than 1:1, and in many instances is from about 1.1 to about 1.6:1.

Alkaline metal salts of perborates are preferably used. The most preferred salt is the sodium salt. The most preferred perborate salt according to the invention for economic reasons is sodium perborate monohydrate.

Perborate is employed in the inventive compositions in amounts of from about 1% to about 44% (amount calculated including water of hydration, if any). Preferably due to the advantage of the inventive composition to increase the solubility of perborate in the water/polyol system, the inventive compositions include a perborate salt in amounts which are above the soluble amount of perborate in pure water. Such amount would depend on the relative amounts of the perborate, the polyol and water. The inventive compositions preferably include more than 1.5% of the perborate salt, especially when the salt is sodium perborate monohydrate. The preferred inventive compositions include from about 1.5 to about 20% of the perborate, most preferably from 2 to 8%.

Although one of the advantages of the inventive composition is the increased solubility of perborate in aqueous compositions, the inventive compositions do not necessarily need to contain all the perborate in solution. Some perborate in the inventive compositions may be in undissolved form, may be in the form of suspended particles and/or encapsulated particles.

Preferably at least 80% of the total perborate in the inventive compositions, most preferably from 85 to 100%, optimally from 90 to 100% is in the solubilized form.

The compositions preferably comprise available oxygen (hereinafter also sometimes mentioned as AvOx), preferably, supplied predominantly by the perborate, in an amount of from 0.1 to 10%, preferably from 0.2 to 5%, and most preferably from 0.3 to 2%. In the most preferred compositions the available oxygen is provided by the solubilized perborate.

It should be noted that "available oxygen" as used herein denotes total available oxygen, i.e all the oxygen that is produced from the perborate, since in the course of the measurement all the peroxo compounds (including perborate and peroxide) are consumed.

Stability of Compositions

The available oxygen in the inventive compositions is stable (surprisingly, since the compositions are aqueous) to a substantially greater extent than peroxide in aqueous compositions. Generally, the inventive compositions are substantially stable for at least 1 week at 40° C., preferably for at least 4 weeks at 40° C., and most preferably for at least 26 weeks at 25° C.

By "substantially stable", it is meant that the inventive compositions retain at least 35%, preferably 50%, and most preferably at least 75% of initial available oxygen.

Measurement of Available Oxygen

The concentration of available oxygen can be measured by chemical titration methods known in the art, such as the iodometric method, thiosulphatimetric method, the permanganometric method and the cerimetric method. Said methods and the criteria for the choice of the appropriate method are described for example in "Hydrogen Peroxide", W. C. Schumb, C. N. Satterfield and R. L. Wentworth, Reinhodl Publishing Corporation, new Yor, 1955 and "Organic Peroxides", Daniel Swern, Editor Wiley Int. Science, 1970. The specific method employed herein is described more fully in Example 2 hereinbelow.

Polyol

The polyols which can be used in the present invention contain C-, H- and O-atoms. These polyols contain at least 2 hydroxy groups, preferably from 2 to 6 hydroxy groups. Typical examples of polyols particularly suitable for use in the present invention are diols such as 1,2 propane diol, ethylene glycol, erythritan, and polyols such as glycerol, sorbitol, mannitol, glucose, fructose, lactose, etc.

Sorbitol and glycerol are preferred polyols, due to their ready availability.

Polyol is included in the inventive compositions to enhance the solubility of perborate. The amount of polyol is determined by the amount of the perborate salt and the amount of water in the composition. Thus, polyol is generally employed in an amount of from 1 to about 44% preferably from 2 to 25%, optimally from 3 to 10%. While not wishing to be bound by this theory, it is contemplated that the presence of polyol increases the solubility of perborate in water due to the formation of the complex between perborate and polyol which is more soluble than the perborate molecule alone. In any event, to maximize the advantages of the invention, perborate and polyol are employed in the molar ratio of from 1:10 to 10:1, preferably from 1:5 to 5:1, most preferably from 1:2 to 2:1.

Water

The aqueous bleach composition of the invention generally includes from 55 to 98% of water, preferably from 60 to 80%, more preferably from 60 to 70%. The water amount does not include bound water (water of hydration).

pH

Generally, the inventive compositions may be formulated at any pH. The particular advantage of the inventive compositions, however is that they stably retain available oxygen in aqueous solutions even at pH 5 and higher—the pH range which is particularly detrimental to the stability of hydrogen peroxide in water.

Furthermore, it has been discovered as part of the present invention that the inventive compositions provide surprisingly effective pH jump on dilution with water, a more effective pH jump than in the corresponding borax/polyol system. In the preferred compositions, the initial pH of the inventive compositions is in the range of from 5 to 7, which upon dilution with water (at least 3 times the amount of water), increases by at least 2 units.

Thus, the preferred inventive compositions have the pH of at least 5, preferably the pH of from 5.5 to 9, most preferably from 6 to 7.5.

Use of the Composition

The inventive composition may be used as a bleaching composition, whenever bleaching action is desired, to bleach stains or surfaces such as hard surfaces, fabrics, hair, teeth and skin. The preferred use of the composition is for laundry. The composition may be used alone, or in combination with other compositions, such as a detergent composition comprising a surfactant. When used alone, the typical use of the composition is to add the inventive composition as a booster to an aqueous bath containing laundry in a laundry machine, or as a pretreatment for soiled fabrics prior to their washing in a laundry machine. Alternatively, the inventive compositions may optionally be formulated as full detergent compositions including one or more of the optional ingredients discussed hereinbelow and such compositions may be used alone, without additional detergent compositions, for washing soiled fabric, upon their addition to the aqueous bath in the laundry machine containing laundry or for pre-treating fabrics and/or stains. The perborate in the inventive compositions reduces chlorine in the tap water, minimizing or eliminating the yellowing of fabrics upon repeated laundry cycles.

Process of Making the Composition

The inventive composition may be made by simply mixing the ingredients. In a preferred method of making the composition especially when the composition comprises further optional ingredients as described hereinbelow.

The preferred process for making the inventive bleach composition is as follows: addition of water, polyol, and optional builder with agitation to obtain a solution, followed by addition of perborate while stirring until a clear solution is formed.

The preferred process for formulating a full laundry composition is as follows: Water is divided into two portions. Three-quarters of the water is used in a main mix, and the remaining water is used in the premix so as to form a solution. The preferred process involves the creation of a main mix by combining the first portion of water with the major surfactants in the formulation and agitating. Next a premix is prepared from the perborate, polyol and the remaining water in the presence of an optional builder, e.g. citric acid. The prepared premix is added to the main mix at a temperature below 40° C. to give the formulated product. The preferable order of addition when making the premix is to first add water, polyol, and builder with agitation, followed by addition of the perborate salt while stirring until a clear solution is formed.

Optional Ingredients

Builders/Electrolytes

A particularly preferred ingredient of the inventive compositions is a builder, in order to sequester transition metals and remove hardness. Builders which can be used according to this invention include conventional alkaline detergency builders, inorganic or organic, which should be used at levels from about 0.1% to about 20.0% by weight of the composition, preferably from 1.0% to about 10.0% by weight, more preferably 2% to 5% by weight.

As electrolyte may be used any water-soluble salt. Electrolyte may also be a detergency builder, such as the inorganic builder sodium tripolyphosphate, or it may be a non-functional electrolyte such as sodium sulphate or chloride. Preferably the inorganic builder comprises all or part of the electrolyte. That is the term electrolyte encompasses both builders and salts.

Examples of suitable inorganic alkaline detergency builders which may be used are water-soluble alkalimetal phosphates, polyphosphates, borates, silicates and also carbonates. Specific examples of such salts are sodium and potassium triphosphates, pyrophosphates, orthophosphates, hexametaphosphates, tetraborates, silicates and carbonates.

Examples of suitable organic alkaline detergency builder salts are: (1) water-soluble amino polycarboxylates, e.g., sodium and potassium ethylenediaminetetraacetates, nitrilotriacetatesand N-(2 hydroxyethyl)-nitrilodiacetates; (2) water-soluble salts of phytic acid, e.g., sodium and potassium phytates (see U.S. Pat. No. 2,379,942); (3) water-soluble polyphosphonates, including specifically, sodium, potassium and lithium salts of ethane-1-hydroxy-1,1-diphosphonic acid; sodium, potassium and lithium salts of methylene diphosphonic acid; sodium, potassium and lithium salts of ethylene diphosphonic acid; and sodium, potassium and lithium salts of ethane-1,1,2-triphosphonic acid. Other examples include the alkali metal salts of ethane-2-carboxy-1,1-diphosphonic acid hydroxymethanediphosphonic acid, carboxyldiphosphonic acid, ethane-1-hydroxy-1,1,2-triphosphonic acid, ethane-2-hydroxy-1,1,2-triphosphonic acid, propane-1,1,3,3-tetraphosphonic acid, propane-1,1,2,3-tetraphosphonic acid, and propane-1,2,2,3-tetraphosphonic acid; (4) water-soluble salts of polycarboxylate polymers and copolymers as described in U.S. Pat. No. 3,308,067.

In addition, polycarboxylate builders can be used satisfactorily, including water-soluble salts of mellitic acid, citric acid, and carboxymethyloxysuccinic acid, imino disuccinate, salts of polymers of itaconic acid and maleic acid, tartrate monosuccinate, tartrate disuccinate and mixtures thereof.

Sodium citrate is particularly preferred, to optimize the function vs. cost, (e.g. from 0 to 15%, preferably from 1 to 10%).

Certain zeolites or aluminosilicates can be used. One such aluminosilicate which is useful in the compositions of the invention is an amorphous water-insoluble hydrated compound of the formula $Na_x[(AlO_2)_y \cdot SiO_2]$, wherein x is a number from 1.0 to 1.2 and y is 1, said amorphous material being further characterized by a $Mg^{2+}$ exchange capacity of from about 50 mg eq. $CaCO_3$/g. and a particle diameter of from about 0.01 micron to about 5 microns. This ion exchange builder is more fully described in British Pat. No. 1,470,250.

A second water-insoluble synthetic aluminosilicate ion exchange material useful herein is crystalline in nature and has the formula $Na_z[(AlO_2)_y \cdot (SiO_2)]xH_2O$, wherein z and y are integers of at least 6; the molar ratio of z to y is in the range from 1.0 to about 0.5, and x is an integer from about 15 to about 264; said aluminosilicate ion exchange material having a particle size diameter from about 0.1 micron to about 100 microns; a calcium ion exchange capacity on an anhydrous basis of at least about 200 milligrams equivalent of $CaCO_3$ hardness per gram; and a calcium exchange rate on an anhydrous basis of at least about 2 grains/gallon/minute/gram. These synthetic aluminosilicates are more fully described in British Patent No. 1,429,143.

Surfactant

The compositions of the invention, especially fully formulated laundry detergent compositions, may contain one or more surface active agents selected from the group consisting of anionic, nonionic, cationic, ampholytic and zwitterionic surfactants or mixtures thereof. The preferred surfactant detergents for use in the present invention are mixtures of anionic and nonionic surfactants although it is to be understood that any surfactant may be used alone or in combination with any other surfactant or surfactants.

Anionic Surfactant Detergents

Anionic surface active agents which may be used in the present invention are those surface active compounds which contain a long chain hydrocarbon hydrophobic group in their molecular structure and a hydrophile group, i.e. water solubilizing group such as carboxylate, sulfonate or sulfate group or their corresponding acid form. The anionic surface active agents include the alkali metal (e.g. sodium and potassium) water soluble higher alkyl aryl sulfonates, alkyl sulfonates, alkyl sulfates and the alkyl poly ether sulfates. They may also include fatty acid or fatty acid soaps. One of the preferred groups of anionic surface active agents are the alkali metal, ammonium or alkanolamine salts of higher alkyl aryl sulfonates and alkali metal, ammonium or alkanolamine salts of higher alkyl sulfates. Preferred higher alkyl sulfates are those in which the alkyl groups contain 8 to 26 carbon atoms, preferably 12 to 22 carbon atoms and more preferably 14 to 18 carbon atoms. The alkyl group in the alkyl aryl sulfonate preferably contains 8 to 16 carbon atoms and more preferably 10 to 15 carbon atoms. A particularly preferred alkyl aryl sulfonate is the sodium potassium or ethanolamine $C_{10}$ to $C_{16}$ benzene sulfonate, e.g. sodium linear dodecyl benzene sulfonate. The primary and secondary alkyl sulfates can be made by reacting long chain alpha-olefins with sulfites or bisulfites, e.g. sodium bisulfite. The alkyl sulfonates can also be made by reacting long chain normal paraffin hydrocarbons with sulfur dioxide and oxygen as describe in U.S. Pat. Nos. 2,503,280, 2,507,088, 3,372,188 and 3,260,741 to obtain normal or secondary higher alkyl sulfates suitable for use as surfactant detergents.

The alkyl substituent is preferably linear, i.e. normal alkyl, however, branched chain alkyl sulfonates can be employed, although they are not as good with respect to biodegradability. The alkane, i.e. alkyl, substituent may be terminally sulfonated or may be joined, for example, to the 2-carbon atom of the chain, i.e. may be a secondary sulfonate. It is understood in the art that the substituent may be joined to any carbon on the alkyl chain. The higher alkyl sulfonates can be used as the alkali metal salts, such as sodium and potassium. The preferred salts are the sodium salts. The preferred alkyl sulfonates are the $C_{10}$ to $C_{18}$ primary normal alkyl sodium and potassium sulfonates, with the $C_{10}$ to $C_{15}$ primary normal alkyl sulfonate salt being more preferred.

Mixtures of higher alkyl benzene sulfonates and higher alkyl sulfates can be used as well as mixtures of higher alkyl benzene sulfonates and higher alkyl polyether sulfates.

The alkali metal or ethanolamine alkyl aryl sulfonate can be used in an amount of 0 to 43%, preferably 5 to 35% and more preferably 5 to 15% by weight.

The alkali metal or ethanolamine sulfate can be used in admixture with the alkylbenzene sulfonate in an amount of 0 to 43%, preferably 5 to 35% by weight.

Also normal alkyl and branched chain alkyl sulfates (e.g., primary alkyl sulfates) may be used as the anionic component.

The higher alkyl polyethoxy sulfates used in accordance with the present invention can be normal or branched chain alkyl and contain lower alkoxy groups which can contain two or three carbon atoms. The normal higher alkyl polyether sulfates are preferred in that they have a higher degree of biodegradability than the branched chain alkyl and the lower poly alkoxy groups are preferably ethoxy groups.

The preferred higher alkyl polyethoxy sulfates used in accordance with the present invention are represented by the formula:

$R^1$—O(CH$_2$CH$_2$O)$_p$—SO$_3$M, where $R^1$ is $C_8$ to $C_{20}$ alkyl, preferably $C_{10}$ to $C_{18}$ and more preferably $C_{12}$ to $C_{15}$; p is 2 to 8, preferably 2 to 6, and more preferably 2 to 4; and M is an alkali metal, such as sodium and potassium, or an ammonium cation. The sodium and potassium salts are preferred.

A preferred higher alkyl poly ethoxylated sulfate is the sodium salt of a triethoxy $C_{12}$ to $C_{15}$ alcohol sulfate having the formula:

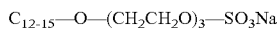
$C_{12-15}$—O—(CH$_2$CH$_2$O)$_3$—SO$_3$Na

Examples of suitable alkyl ethoxy sulfates that can be used in accordance with the present invention are $C_{12-15}$ normal or primary alkyl triethoxy sulfate, sodium salt; n-decyl diethoxy sulfate, sodium salt; $C_{12}$ primary alkyl diethoxy sulfate, ammonium salt; $C_{12}$ primary alkyl triethoxy sulfate, sodium salt; $C_{15}$ primary alkyl tetraethoxy sulfate, sodium salt; mixed $C_{14-15}$ normal primary alkyl mixed tri- and tetraethoxy sulfate, sodium salt; stearyl pentaethoxy sulfate, sodium salt; and mixed $C_{10-18}$ normal primary alkyl triethoxy sulfate, potassium salt.

The normal alkyl ethoxy sulfates are readily biodegradable and are preferred. The alkyl poly-lower alkoxy sulfates can be used in mixtures with each other and/or in mixtures with the above discussed higher alkyl benzene, sulfonates, or alkyl sulfates.

The alkali metal higher alkyl poly ethoxy sulfate can be used with the alkylbenzene sulfonate and/or with an alkyl sulfate, in an amount of 0 to 43%, preferably 5 to 35% and more preferably 5 to 20% by weight of the entire composition.

Nonionic Surfactant

Nonionic surfactants which can be used with the invention, alone or in combination with other surfactants are described below.

As is well known, the nonionic surfactants are characterized by the presence of a hydrophobic group and an organic hydrophilic group and are typically produced by the condensation of an organic aliphatic or alkyl aromatic hydrophobic compound with ethylene oxide (hydrophilic in nature). Typical suitable nonionic surfactants are those disclosed in U.S. Pat. Nos. 4,316,812 and 3,630,929, incorporated by reference herein.

Usually, the nonionic surfactants are polyalkoxylated lipophiles wherein the desired hydrophile-lipophile balance is obtained from addition of a hydrophilic poly-lower alkoxy group to a lipophilic moiety. A preferred class of nonionic detergent is the alkoxylated alkanols wherein the alkanol is of 9 to 20 carbon atoms and wherein the number of moles of alkylene oxide (of 2 or 3 carbon atoms) is from 3 to 20. Of such materials it is preferred to employ those wherein the alkanol is a fatty alcohol of 9 to 11 or 12 to 15 carbon atoms and which contain from 5 to 8 or 5 to 9 alkoxy groups per mole. Also preferred is paraffin—based alcohol (e.g. nonionics from Huntsman or Sassol).

Exemplary of such compounds are those wherein the alkanol is of 10 to 15 carbon atoms and which contain about 5 to 12 ethylene oxide groups per mole, e.g. Neodol® 25-9 and Neodol® 23-6.5, which products are made by Shell Chemical Company, Inc. The former is a condensation product of a mixture of higher fatty alcohols averaging about 12 to 15 carbon atoms, with about 9 moles of ethylene oxide and the latter is a corresponding mixture wherein the carbon atoms content of the higher fatty alcohol is 12 to 13 and the number of ethylene oxide groups present averages about 6.5. The higher alcohols are primary alkanols. Another subclass of alkoxylated surfactants which can be used contain a precise alkyl chain length rather than an alkyl chain distribution of the alkoxylated surfactants described above. Typically, these are referred to as narrow range alkoxylates. Examples of these include the Neodol-1® series of surfactants manufactured by Shell Chemical Company.

Other useful nonionics are represented by the commercially well known class of nonionics sold under the trademark Plurafacs® by BASF. The Plurafacs® are the reaction products of a higher linear alcohol and a mixture of ethylene and propylene oxides, containing a mixed chain of ethylene oxide and propylene oxide, terminated by a hydroxyl group. Examples include $C_{13}$–$C_{15}$ fatty alcohol condensed with 6 moles ethylene oxide and 3 moles propylene oxide, $C_{13}$–$C_{15}$ fatty alcohol condensed with 7 moles propylene oxide and 4 moles ethylene oxide, $C_{13}$–$C_{15}$ fatty alcohol condensed with 5 moles propylene oxide and 10 moles ethylene oxide or mixtures of any of the above.

Another group of liquid nonionics are commercially available from Shell Chemical Company, Inc. under the Dobanol® or Neodol® trademark: Dobanol® 91-5 is an ethoxylated $C_9$–$C_{11}$ fatty alcohol with an average of 5 moles ethylene oxide and Dobanol® 25-7 is an 15 ethoxylated $C_{12}$–$C_{15}$ fatty alcohol with an average of 7 moles ethylene oxide per mole of fatty alcohol.

In the compositions of this invention, preferred nonionic surfactants include the $C_{12}$–$C_{15}$ primary fatty alcohols with relatively narrow contents of ethylene oxide in the range of from about 6 to 9 moles, and the $C_9$ to $C_{11}$ fatty alcohols ethoxylated with about 5–6 moles ethylene oxide.

Another class of nonionic surfactants which can be used in accordance with this invention are glycoside surfactants. Glycoside surfactants suitable for use in accordance with the present invention include those of the formula:

wherein R is a monovalent organic radical containing from about 6 to about 30 (preferably from about 8 to about 18) carbon atoms; $R^1$ is a divalent hydrocarbon radical containing from about 2 to 4 carbons atoms; O is an oxygen atom; y is a number which can have an average value of from 0 to about 12 but which is most preferably zero; Z is a moiety derived from a reducing saccharide containing 5 or 6 carbon atoms; and x is a number having an average value of from 1 to about 10 (preferably from about 1½ to about 10).

A particularly preferred group of glycoside surfactants for use in the practice of this invention includes those of the formula above in which R is a monovalent organic radical (linear or branched) containing from about 6 to about 18 (especially from about 8 to about 18) carbon atoms; y is zero; z is glucose or a moiety derived therefrom; x is a number having an average value of from 1 to about 4 (preferably from about 1½ to 4).

Nonionic surfactants which may be used include polyhydroxy amides as discussed in U.S. Pat. No. 5,312,954 to Letton et al. and aldobionarnides such as disclosed in U.S. Pat. No. 5,389,279 to Au et al., both of which are hereby incorporated by reference into the subject application.

Generally, nonionics may comprise 0 to 43% by wt., preferably 5 to 35%, more preferably 5 to 25% by wt. of the composition.

Mixtures of two or more of the nonionic surfactants can be used.

Cationic Surfactants

Many cationic surfactants are known in the art, and almost any cationic surfactant having at least one long chain alkyl group of about 10 to 24 carbon atoms is suitable in the present invention. Such compounds are described in "Cationic Surfactants", Jungermann, 1970, incorporated by reference. Specific cationic surfactants which can be used as surfactants in the subject invention are described in detail in U.S. Pat. No. 4,497,718, hereby incorporated by reference.

As with the nonionic and anionic surfactants, the compositions of the invention may use cationic surfactants alone or in combination with any of the other surfactants known in the art. Of course, the compositions may contain no cationic surfactants at all.

Amphoteric Surfactants

Ampholytic synthetic surfactants can be broadly described as derivatives of aliphatic or aliphatic derivatives of heterocyclic secondary and tertiary amines in which the aliphatic radical may be straight chain or branched and wherein one of the aliphatic substituents contains from about 8 to 18 carbon atoms and at least one contains an anionic water-soluble group, e.g. carboxylate, sulfonate, sulfate. Examples of compounds falling within this definition are sodium 3-(dodecylamino)propionate, sodium 3-(dodecylamino) propane-1-sulfonate, sodium 2-(dodecylamino)ethyl sulfate, sodium 2-(dimethylamino) octadecanoate, disodium 3-(N-carboxymethyldodecylamino)propane 1-sulfonate, disodium octadecyl-imminodiacetate, sodium 1-carboxymethyl-2-undecylimidazole, and sodium N,N-bis (2-hydroxyethyl) 2-sulfato-3-dodecoxypropylamine. Sodium 3-(dodecylamino) propane-1-sulfonate is preferred.

Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. The cationic atom in the quaternary compound can be part of a heterocyclic ring. In all of these compounds there is at least one aliphatic group, straight chain or branched, containing from about 3 to 18 carbon atoms and at least one aliphatic substituent containing an anionic water-solubilizing group, e.g., carboxy, sulfonate, sulfate, phosphate, or phosphonate.

Specific examples of zwitterionic surfactants which may be used are set forth in U.S. Pat. No. 4,062,647, hereby incorporated by reference.

The amount of surfactant used may vary from 1 to 43% by weight, preferably 5 to 40% by weight, most preferably from 5 to 35%, optimally from 10 to 30%.

As noted the preferred surfactant systems of the invention are mixtures of anionic and nonionic surfactants.

Particularly preferred systems include, for example, mixtures of linear alkyl aryl sulfonates (LAS) and linear alkoxylated (e.g., ethoxylated) sulfates (AES) with alkoxylated nonionics for example in the ratio of 1:2:1 (i.e., 5:1, preferably 3:1 anionic to nonionic).

Preferably, the nonionic should comprise, as a percentage of an anionic/nonionic system, at least 20%, more preferably at least 25%, up to about 75% of the total surfactant system. A particularly preferred surfactant system comprises anionic:nonionic in a ratio of 3:1.

Hydrotropes

In general, addition of hydrotropes helps to incorporate higher levels of surfactants into isotropic liquid detergents than would otherwise be possible due to phase separation of surfactants from the aqueous phase. Hydrotropes also allow a change in the proportions of different types of surfactants, namely anionic, nonionic, cationic and zwitterionic, without encountering the problem of phase separation. Thus, they increase the formulation flexibility. Hydrotropes function through either of the following mechanisms: i) they increase the solubility of the surfactant in the aqueous phase by changing the solvent power of the aqueous phase; short chain alcohols such as ethanol, isopropanol and also glycerol and propylene glycol are examples in this class and ii) they prevent formation of liquid crystalline or lamellar phases of surfactants by disrupting the packing of the hydrocarbon chains of the surfactants in the micelles; alkali metal salts of alkyl aryl sulfonates such as xylene sulfonate, cumene sulfonate and alkyl aryl disulfonates such as DOWFAX® family of hydrotropes marketed by Dow Chemicals are examples in this class.

Other types of suitable hydrotropes include low molecular weight alkyl sulfates (e.g., octylsulfate).

Preferred hydrotropes in the compositions of the present invention are polyols, which may also act as enzyme stabilizers, such as propylene glycol, ethylene glycol, glycerol, sorbitol, mannitol and glucose.

In general, hydrotropes may be present in an amount of about 1% to 25% by wt., preferably 1% to 10% by wt. of the composition.

Although the inventive compositions function as effective pH jump systems, additional pH jump systems such as borax/polyol or boric acid/polyol may be present.

Alkalinity buffers which may be added to the compositions of the invention include monoethanolamine, triethanolamine, borax and the like.

Other materials such as clays, particularly of the water-insoluble types, may be useful adjuncts in compositions of this invention. Particularly useful is bentonite. This material is primarily montmorillonite which is a hydrated aluminum silicate in which about ⅙ th of the aluminum atoms may be replaced by magnesium atoms and with which varying anounts of hydrogen, sodium, potassium, calcium, etc. may be loosely combined. The bentonite in its more purified form (i.e. free from any grit, sand, etc.) suitable for detergents contains at least 50% montmorillonite and thus its cation exchange capacity is at least about 50 to 75 meq per 100 g of bentonite. Particularly preferred bentonites are the Wyoming or Western U.S. bentonites which have been sold as Thixo-jels 1, 2, 3 and 4 by Georgia Kaolin Co. These bentonites are known to soften textiles as described in British Patent No. 401, 413 to Marriott and British Patent No. 461,221 to Marriott and Guam.

In addition, various other detergent additives or adjuvants may be present in the detergent product to give it additional desired properties, either of functional or aesthetic nature.

There also may be included in the formulation, minor amounts of soil suspending or anti-redeposition agents, e.g. polyvinyl alcohol, fatty amides, sodium carboxymethyl cellulose, hydroxy-propyl methyl cellulose. A preferred anti-redeposition agent is sodium carboxylmethyl cellulose having a 2:1 ratio of CM/MC which is sold under the tradename Relatin DM 4050.

Optical brighteners for cotton, polyamide and polyester fabrics can be used. Suitable optical brighteners include Tinopal® LMS-X, Tinopal® CBS-X, stilbene, triazole and benzidine sulfone compositions, especially sulfonated substituted triazinyl stilbene, sulfonated naphthotriazole stilbene, benzidene sulfone, etc. Most preferred are UV/stable brighteners (for compositions visible in transparent containers), such as distyrylbiphenyl derivatives (Tinopal® CBS-X).

Anti-foam agents, e.g. silicon compounds, such as Silicane® L 7604, can also be added in small effective amounts.

Bactericides, e.g. tetrachlorosalicylanilide and hexachlorophene, fungicides, dyes, pigments (water dispersible), preservatives, e.g. formalin, ultraviolet absorbers, anti-yellowing agents, such as sodium carboxymethyl cellulose, pH modifiers and pH buffers, color safe bleaches, perfume and dyes and bluing agents such as Iragon Blue L2D, Detergent Blue 472/572 and ultramarine blue can be used.

Also, additional soil release polymers and cationic softening agents may be used.

Preferably, the detergent composition is a colored composition packaged in the transparent/translucent ("see-through") container.

Container

Preferred containers are opaque bottles. The container of the present invention may be of any form or size suitable for storing and packaging liquids for household use. For example, the container may have any size but usually the container will have a maximal capacity of 0.05 to 15 L, preferably, 0.1 to 5 L, more preferably from 0.2 to 2.5 L. Preferably, the container is suitable for easy handling. For example the container may have handle or a part with such dimensions to allow easy lifting or carrying the container with one hand. The container preferably has a means suitable for pouring the liquid detergent composition and means for reclosing the container. The pouring means may be of any size of form but, preferably will be wide enough for convenient dosing the liquid detergent composition. The closing means may be of any form or size but usually will be screwed or clicked on the container to close the container. The closing means may be cap which can be detached from the container. Alternatively, the cap can still be attached to the container, whether the container is open or closed. The closing means may also be incorporated in the container. The following specific examples further illustrate the invention, but the invention is not limited thereto.

EXAMPLE 1

This example demonstrates the substantial solubility enhancement of perborate in water, in the presence of polyol.

An iterative process was used to determine the extent of perborate solubilty in water and polyol/water. 1.5g of Na perborate monohydrate was added either to 100 g of water (Table 1A) or to 90g water and 10g sorbitol (70% active) (Table 1B). The mixture was stirred until all of sodium perborate monohydrate was dissolved. A 0.5g aliquot of sodium perborate monohydrate was then added to the solution while stirring and visually monitored to see if all the added sodium perborate monohydrate dissolves. If the aliquot dissolved, another 0.5g of sodium perborate monohydrate would be added. This procedure was continued until the added perborate no longer appeared to dissolve. The results that were obtained are summarized in Tables 1A and 1B.

TABLE 1A

| Ingredient | Weight (g) | Appearance | pH |
|---|---|---|---|
| Water | 100 | Clear liquid | 5.96 |
| Sodium Perborate monohydrate | 1.5 | Clear solution | 10.00 |
| Sodium Perborate monohydrate | 2.0 | Precipitate formed | 10.06 |

TABLE 1B

| Ingredient | Weight (g) | Molar ratio (perborate/sorbitol) | Appearance | pH |
|---|---|---|---|---|
| Water | 90.0 | | Clear liquid | 5.30 |
| Sorbitol (70%) | 10.0 | | Clear liquid | n.a. |
| Sodium Perborate monohydrate | 1.50 | 1/3.55 | Clear solution | 8.30 |
| Sodium Perborate monohydrate | 3.50 | 1/1.01 | Clear solution | 9.33 |
| Sodium Perborate monohydrate | 5.50 | 1.43/1 | Clear solution | 9.56 |

TABLE 1B-continued

| Ingredient | Weight (g) | Molar ratio (perborate/sorbitol) | Appearance | pH |
|---|---|---|---|---|
| Sodium Perborate monohydrate | 8.00 | 2.09/1 | Clear solution | 9.60 |
| Sodium Perborate monohydrate | 8.50 | 2.22/1 | Precipitate formed | 9.60 |
| Sodium Perborate monohydrate | 9.50 | 2.49/1 | Precipitate formed | 9.60 |

It can be seen from the results in Table IA that the solubility of sodium perborate monohydrate in water was below 2.0g in water.

By contrast, it can be seen from the results in Table 1B that the solubility of sodium perborate monohydrate in water, in the presence of polyol was up to 8.5g, thus demonstrating that a polyol increased the solubility of perborate (about 400%) in an aqueous environment. Furthermore, the pH of this system was lower than the corresponding aqueous solution without any polyol, suggesting the formation of a complex between the polyol and the perborate. If the polyol concentration were higher, then the perborate solubility limit would be also increased even above 8%.

EXAMPLE 2

This example illustrates fully formulated laundry products of the invention. Table 2A below summarizes the compositions: Compositions 1–4 were gels and Composition 5 was an isotropic liquid.

The examples were prepared by first mixing three-quarters of the total water, propylene glycol, 50% sodium hydroxide solution (if any), monoethanol amine to create a main mix. Sulfonic acid and coconut fatty acid (if the latter was an ingredient in the formulation) were added to the main mix. The mixing was continued until both acids were fully dispersed and neutralized or the alkaline neutralizing agents were fully consumed. A premix was then prepared by mixing one-quarter of the total water, 70% sorbitol, sodium perborate monohydrate, citric acid, and EDTA. Subsequently, nonionic surfactant was added into the main mix with agitation. Then the premix was added and mixing was continued until a homogeneous product was formed.

The stability of bleaching species in these mixtures was monitored with over time by a potentiometric titration with potassium permanganate. The results are reported in terms of Available Oxygen Content, or AvOx, which describes the ability of a bleaching species to provide peroxide.

All available oxygen (AvOx) titrations were conducted using an autotitrator (Metrohm 751GDP Titrino) equipped with a Pt Titrode electrode (Metrohm # 6.0431.100). Samples were measured by the following protocol:

A 1.000g test sample was weighed into a 250 mL beaker and diluted with 50 mL of 20% sulfuric acid and 50 mL water. The resulting mixture was titrated with an enough 0.1 N potassium permanganate to achieve the potentiometric endpoint for the system. The procedure was repeated using a blank sample to compensate for any reactive components in the reagents used for the assay.

The results that were obtained are summarized in Tables 2A and 2B.

TABLE 2A

| Ingredients | 1 | 2 | 3 | 4 | 5 |
|---|---|---|---|---|---|
| Linear Alkyl Benzene Sulphonic Acid | 5.73 | 5.73 | 5.73 | 5.73 | 10.5 |
| Nonionic (C12–C14, 9 EO) | 6.0 | 6.0 | 6.0 | 6.0 | 5.0 |
| Coco fatty acid | 6.0 | 6.0 | 4.0 | 4.0 | 0 |
| Sorbitol (70% active) | 7.9 | 7.9 | 6.0 | 6.0 | 6 |
| Propylene glycol | 1.0 | 1.0 | 1.0 | 1.0 | 1.0 |
| NaOH (50% active) | 0 | 1.15 | 0 | 0 | 1.0 |
| Monoethanolamine | 0.88 | 0.88 | 0.58 | 0.47 | 0 |
| Citric acid | | 0.80 | 1.0 | 1.0 | 1.0 |
| Sodium Perborate monohydrate | 5.00 | 4.4 | 3.5 | 4.0 | 4.50 |
| EDTA.2H2O | | 0.30 | 0.10 | 0.10 | 0.10 |
| Water | 65.86 | 65.38 | 71.45 | 71.05 | 70.05 |
| Miscellaneous | To 100 | To 100 | To 100 | To 100 | To 100 |
| Perborate/polyol molar ratio | 1.15/1 | 1/1 | 1/1.03 | 1.11/1 | 1.25/1 |
| pH | 6.24 | 7.37 | 5.69 | 6.24 | 5.40 |

TABLE 2B

Stability of Fully Formulated Bleaching Gels and Liquids at 25° C.

% Available Oxygen (Fraction of Initial Remaining)

| Storage Time | 1 | 2 | 3 | 4 | 5 |
|---|---|---|---|---|---|
| Initial | 0.76 (100%) | 0.67 (100%) | 0.53 (100%) | 0.61 (100%) | 0.79 (100%) |
| Two months | 0.68 (89.1%) | 0.57 (85.0%) | | | |
| Three months | 0.50 (66.3%) | 0.37 (55.0%) | 0.36 (67.2%) | 0.56 (91.7%) | 0.78 (98.4%) |

It can be seen from Table 2A that fully formulated aqueous laundry products containing relatively high amounts of dissolved perborate could be achieved. It can be seen from the results in Table 2B that the products were surprisingly stable on storage at 25° C.

EXAMPLE 3

This example investigated "pH jump" in the formulated samples by preparing a 0.22% (wt/wt) solution and measuring the pH of the dilute product against that of a reference (water). Composition 5 was within the scope of the invention, while Comparative Composition A was outside the scope of the invention.

Composition 5 and Comparative composition A were prepared by the method described in Example 2, except that Comparative composition A was prepared by use of borax to replace sodium perborate monohydrate in premix.

The results that were obtained are summarized in Table 3 below.

TABLE 3

| Ingredients | Composition 5 | Comparative Composition A |
|---|---|---|
| Linear Alkyl Benzene Sulphonic acid | 10.50 | 10.50 |
| Nonionic (C12–C14, 9 EO) | 5.0 | 5.0 |
| Sorbitol (70% active) | 6.0 | 6.0 |
| Borax | 0 | 4.50 |
| Propylene glycol | 1.0 | 1.0 |
| NaOH (50% active) | 1.0 | 1.0 |
| Citric acid | 1.0 | 1.0 |
| Sodium Perborate monohydrate | 4.50 | 0 |
| EDTA.2$H_2O$ | 0.10 | 0.10 |
| Water | 70.05 | 70.05 |
| Miscellaneous | To 100 | To 100 |
| pH (neat solution) | 6.11 | 6.20 |
| pH (0.22% solution) | 8.38 | 7.75 |
| Water pH (reference) | 5.95 | 5.95 |
| ΔpH | 2.43 | 1.80 |

As can be seen from Table 3, both compositions exhibit a pH jump. However, the perborate/sorbitol system (Composition 5) produces a better pH jump than the borax/sorbitol mixture (Comparative Composition A), which theoretically should consume more protons upon dissolution than perborate.

EXAMPLE 4

This example investigated the effectiveness of the perborate/sorbitol mixture at stabilizing the formulation (Composition 6 below, within the scope of the invention) compared to a formulation containing borax/sorbitol/hydrogen peroxide (Comparative Composition B, outside the scope of the invention). Both compositions had the same initial available oxygen level and boron content.

Composition 6 was prepared by first mixing water, propylene glycol and 50% sodium hydroxide solution to create a main mix. While having a moderate agitation, sulfonic acid was added to the main mix. The mixing was continued until the acid was fully dispersed and NaOH was fully consumed, followed by addition of nonionic surfactant. A premix was prepared by mixing remaining water, sorbitol (70% active), sodium perborate monohydrate, citric acid (if any), and EDTA until a homogeneous or clear solution was formed. Subsequently, the premix was added into the main mix with agitation. The mixing was continued until a homogeneous product was formed, followed by adjusting pH to about 7.0 with either NaOH (50/) solution or citric acid monohydrate.

Comparative Composition B was prepared by first mixing water, 70% sorbitol solution, propylene glycol, 50% sodium hydroxide solution and borax to create a main mix. After borax was dissolved under moderate agitation, sulfonic acid was added to the main mix. The mixing was continued until the acid was fully dispersed and NaOH was fully consumed. After the main mix cooled down to around 35° C., $H_2O_2$ (30%) aqueous solution was added. Nonionic surfactant was added to the main mix. The mixing was continued until a homogeneous product was formed; pH was adjusted to about 7.0 with either NaOH (50%) solution or citric acid monohydrate.

The stability of bleaching species in these mixtures was monitored with over time by measuring available oxygen using the method described in Example 2. The results that were obtained are summarized in Tables 5 and 6.

TABLE 4

| Ingredients | Composition 6 | Comparative Composition B |
|---|---|---|
| Premix | | |
| Water | 18.0 | 0 |
| Sorbitol (70% solution) | 6.0 | 0 |
| Sodium Perborate monohydrate | 4 | 0 |
| Main Mix | | |
| Alkyl benzene Sulfonic acid | 10.5 | 10.5 |
| Nonionic (C12–C14, 9 EO) | 5.0 | 5.0 |
| Sorbitol (70% solution) | 6.0 | 6.0 |
| Propylene Glycol | 1.0 | 1.0 |
| Borax | 0 | 2.92 |
| NaOH (50% solution) | 2.06 | 2.06 |
| $H_2O_2$ (30%) | 0 | 4.54 |
| Citric acid monohydrate | Adjust pH | Adjust pH |
| NaOH (50% solution) | adjust pH | adjust pH |
| Water and Miscellaneous | To 100 | To 100 |
| pH | 7.05 | 6.94 |

TABLE 5

Stability at 25° C.

% Available Oxygen (Fraction of Initial Remaining)

| Storage Time | Composition 6 | Comparative Composition B |
|---|---|---|
| 0 Days | 0.72 (100%) | 0.77 (100%) |
| 7 Days | 0.72 (100%) | 0.65 (84.4%) |
| 14 Days | 0.69 (95.8%) | 0.53 (68.8%) |

TABLE 6

Stability at 40° C.

% Available Oxygen (Fraction of Initial Remaining)

| Storage Time | Composition 6 | Comparative Composition B |
|---|---|---|
| 0 Days | 0.72 (100%) | 0.65 (100%) |
| 7 Days | 0.50 (69.4%) | 0.23 (35.4%) |

It can be seen from the results in Tables 5 and 6 that, although both Composition 6 and Comparative Composition B initially had the same available oxygen content and boron content, composition 6 was substantially more stable over time than Comparative Composition B.

What is claimed is:

1. A bleach composition consisting essentially of:
   (a) from about 1% to about 44%, by weight of the composition, of a perborate salt as a source of oxygen bleach;
   (b) from about 1% to about 44%, by weight of the composition, of a polyol, wherein the molar ratio of the perborate salt to the polyol is from about 1:10 to about 10:1;
   (c) water in an amount of at least 55%, by weight of the composition;
   (d) optionally, a builder or an electrolyte; and
   (e) optionally, a surfactant; wherein the composition has an initial pH from 5 to 7.
2. The composition of claim 1, wherein the perborate salt is an alkali metal salt.

3. The composition of claim 1, wherein the available oxygen is from about 0.1% to about 10%, by weight of the composition.

4. The composition of claim 1, wherein the polyol is a vicinal diol.

5. The composition of claim 1, wherein the pH is from 5.5 to 7.

6. The composition of claim 1, wherein the perborate salt forms a clear solution with the water and the polyol.

7. The composition of claim 1, wherein the perborate salt is present in an amount from about 1.5% to about 44%.

8. The composition of claim 1, wherein the builder or electrolyte is present in the composition.

9. The composition of claim 8, wherein the builder is selected from the group consisting of water-soluble amino polycarboxylates, water-soluble salts of phytic acid, water-soluble polyphosphonates, water-soluble salts of polycarboxylate polymers and copolymers, and water-soluble salts of polycarboxylate polymers and copolymers, and water-soluble salts of polycarboxylic acids.

10. The composition of claim 1, wherein the pH of the composition increases upon dilution with water.

11. The composition of claim 1, wherein the available oxygen in the composition remains substantially the same upon storage at 40° C. for at least 1 week.

12. The composition of claim 1 wherein the surfactant is present in the composition.

13. The composition of claim 12 wherein the amount of the surfactant is from about 1 to about 43% by weight of the composition.

14. The composition of claim 1 wherein at least 80% of the total perborate in the composition is in the solubilized form.

15. A method of bleaching a surface selected from the group consisting of fabrics, hard surface, skin, teeth, and hair, the method comprising applying to the surface the composition of claim 1.

16. A method of cleaning laundry, the method comprising contacting laundry in a laundry machine with an aqueous bath comprising the composition of claim 1 and a separate detergent composition comprising a surfactant.

17. A method of cleaning laundry, the method comprising contacting laundry in a laundry machine with an aqueous bath comprising the composition of claim 1.

18. A method of increasing the pH of the composition the method comprising diluting the composition of claim 1 with at least 3 times the amount of water.

19. A method of removing chlorine from tap water, the method comprising mixing tap water with the composition of claim 1.

* * * * *